United States Patent [19]

Hampton et al.

[11] Patent Number: 5,213,738
[45] Date of Patent: May 25, 1993

[54] METHOD FOR MAKING A CAPSULE-SHAPED TABLET

[75] Inventors: Douglas B. Hampton, Holland; George W. Tilton, Grand Haven; Maureen L. Jordan, Allegan, all of Mich.

[73] Assignee: L. Perrigo Company, Allegan, Mich.

[21] Appl. No.: 787,801

[22] Filed: Nov. 4, 1991

Related U.S. Application Data

[62] Division of Ser. No. 523,752, May 15, 1990, Pat. No. 5,089,270.

[51] Int. Cl.⁵ .................................. A61K 9/20
[52] U.S. Cl. .................................. 264/113; 264/112; 425/345
[58] Field of Search .............. 264/112, 113, 129; 425/345, 353

[56] References Cited

U.S. PATENT DOCUMENTS

| | | | |
|---|---|---|---|
| 3,158,109 | 11/1964 | Stott | 107/17 |
| 3,275,519 | 9/1966 | Glassman | 167/82 |
| 3,358,687 | 12/1967 | Miley et al. | 128/271 |
| 4,139,589 | 2/1979 | Beringer et al. | 264/250 |
| 4,353,887 | 10/1982 | Hess et al. | 424/15 |
| 4,591,500 | 5/1986 | Scapinelli | 424/15 |
| 4,820,524 | 4/1989 | Berta | 424/474 |
| 4,921,108 | 5/1990 | Berta | 209/625 |
| 4,990,358 | 2/1991 | Berta | 427/3 |

FOREIGN PATENT DOCUMENTS

1223209 6/1987 Canada.
1123098 9/1956 France.

OTHER PUBLICATIONS

Pharmaceutical Sciences, 1985, pp. 1612–1620.
Remington's, Seventeenth Edition, pp. 443–446.
Pharmazeutischen Industrie, vol. 24, No. 9, 1962, pp. 417–422, Wagner, "Die Praxis der Mantel–und Mehr-schichttablette."

*Primary Examiner*—Mary Lynn Theisen
*Attorney, Agent, or Firm*—Price, Heneveld, Cooper, DeWitt & Litton

[57] ABSTRACT

A method for making a multi-characteristic, bi-layer, capsule-shaped tablet by filling a die with a blend of one or more excipients and one or more active substances, including a first distinguishing ingredient, e.g., a first coloring agent, leveling the first blend and cleaning the die walls above the first blend, adding a second blend including a second distinguishing ingredient, e.g., a second coloring agent, and compressing both blends longitudinally in the die into the shape of a two component capsule. The tablet is coated with a clear coating, such as gelatin, to provide a solid medicament with the appearance of a gelatin capsule.

44 Claims, 3 Drawing Sheets

METHOD FOR MAKING A CAPSULE-SHAPED TABLET

This is a division of application Ser. No. 07/523,752, filed May 15, 1990, now U.S. Pat. No. 5,089,270.

FIELD OF THE INVENTION

The present invention relates to a tablet having the shape and multiple characteristics of a two-piece, hard shell gelatin capsule and its method of manufacture.

BACKGROUND OF THE INVENTION

Drug delivery systems are available in a great variety of shapes and forms, among the most common of which are coated compressed hard tablets, caplets and filled gelatin capsules. The use of gelatin capsules for the encapsulation of medicinal agents has been a popular method for administering drugs because many patients prefer to swallow capsules and caplets rather than tablets.

Caplets are solid, oblong tablets which, although very popular as a drug delivery vehicle, have not reached the same level of consumer acceptance gelatin capsules once had. To solve this problem, the pharmaceutical industry has sought to combine the consumer acceptance of a capsule shape with a caplet. U.S. Pat. No. 4,820,524 relates to a caplet with a two color gelatinous coating to produce a shiny, capsule-like medicament. The disclosed process produces the capsule-like medicaments by individually dipping and drying first one end of each caplet into a first bath of gelatinous coating of one color, and then the other end of each caplet into a second bath of gelatinous coating of a different color. The production of these capsule-like medicaments is reported to be readily facilitated by modifications to existing empty gelatin capsule making equipment. This process of separate dippings to achieve the simulated capsule-like medicament, however, hinders production of these medicaments because it requires an extra dipping and drying step for coating the gelatin onto the caplet.

U.S. Pat. No. 4,591,500 relates to a tablet having the exact shape of a gelatin capsule compressed along the longitudinal or axial direction to form a single transverse ledge at its mid-section instead of extending along the longitudinal axis as in conventional tableting machines, which compress the tablets in the transverse direction. The apparatus disclosed for producing the capsule-shaped tablets consists of a molding device provided with an upper punch and a lower punch of differing longitudinal and lateral dimensions, which creates a ledge or land area where the upper and lower punches come together. A problem inherent in the production of the disclosed tablet by the disclosed apparatus, however, is that the ledge or land area must be at the center of each tablet. This can only be accomplished by compressing the raw materials at the same point in the die to produce each tablet. This is a critical consideration for the production of this product. Further, this reference does not contemplate production of a capsule-type product, i.e., a two colored bi-layer capsule-shaped tablet covered with a coating.

Canadian Patent 1,223,209 relates to a caplet having a capsule shape which is covered with a film coating to simulate both the appearance and function of a gelatin capsule medicament. The disclosed caplet has a body and cap portion in which the outside diameter of the cap portion is greater than the outside diameter of the body portion. The disclosed process produces this shape by compressing powdered material in an appropriately shaped die between appropriately shaped upper and lower punches. The reference advises that the punch edges of the upper and lower tablet punches not be allowed to come in contact with each other during the compression process because this would tend to destroy the punches. A consequence of the procedure, however, is that it forms a seam around the longitudinal equator of the caplet. Therefore, rather than disclosing a medicament with a true capsule shape, the reference discloses a caplet possessing the ledge or step of a capsule, but not the two color appearance of a capsule, nor the cylindrical shape of a capsule.

U.S. Pat. No. 3,158,109 relates to a multi-layer tablet making machine for producing compressed tablets composed of two or more superimposed layers. This patent discloses machines comprising a plurality of dies, each of which successively receives a plurality of powder fills. These first fills are individually precompressed prior to the successive fills entering the die. This precompression of the individual fills reportedly insures a clear delineation between the individual layers in the finished tablets which is clearly visible where powders of different colors are employed for successive fills. This process of making multi-layer tablets discloses compression of the tablets along the smaller dimension of the conventional tablet shapes which are typically made of two different materials.

SUMMARY OF THE INVENTION

The present invention provides for a multicharacteristic, bi-layer, capsule-like tablet consisting of a blend of one or more excipients, one or more active substances, and in one embodiment a first and second different coloring agent compressed along the longitudinal or axial direction into the shape of a two color capsule. The present invention further provides for covering this compressed multi-colored tablet with a clear coating, such as gelatin, to provide a solid medicament with the appearance of a gelatin capsule.

In another embodiment, the present invention provides a bi-layer capsule-like consisting of a first blend of one or more excipients and one or more active substances having a first rate of dissolution and a second blend of one or more excipients and one or more active substances having a second rate of dissolution, compressed along the longitudinal or axial direction into the shape of a capsule. In a preferred embodiment, a first coloring agent is incorporated into the first blend and a second color agent is incorporated into the second blend. In a further preferred embodiment, this multi-dissolution rate compressed tablet can be covered with a clear coating, such as gelatin, to provide a solid medicament with the appearance of a gelatin capsule.

DETAILED DESCRIPTION OF THE INVENTION

Figure 1:
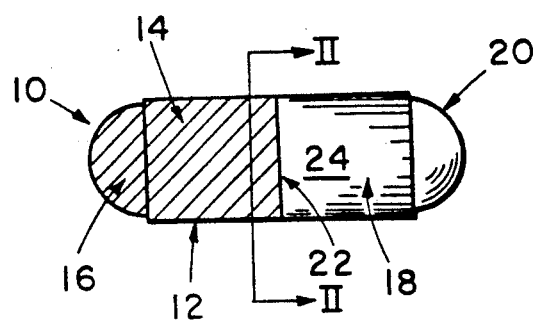
FIG. 1 is a plan view of a coated two color tablet having a capsule-like shape according to the present invention, with the crosshatching indicating a different color rather than a cross section.
Figure 2:
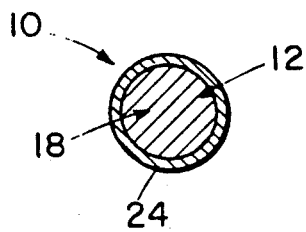
FIG. 2 is a cross-sectional view of the coated tablet taken along section line II—II of FIG. 1.

The present invention provides a coated multiple characteristic, bi-layer tablet 10 (FIG. 1), having a capsule-like shape. The tablet comprises a core 12 consisting of a first body 14 with a first hemispherical cap 16 and a second body 18 with a second hemispherical cap 20. In the first embodiment illustrated, the multiple characteristic comprises different color sections for the tablet which includes a color demarcation line 22 extending transversely between the halves 14 and 18 of the core 12. The core 12 is preferably coated with a clear material 24, as best seen in FIG. 2. The material forming halves 14 and 18 of tablet core 12 have a different characteristic and in a first preferred embodiment are of a different color. Thus, tablet 10 may, for example, be an analgesic such as an acetaminophen product of conventional material except that body 14 is colored differently than body 18. In addition, tablet 10 may be a combination of active substances such as chlorpheniramine maleate in body 14 and phenylpropanolamine hydrochloride in body 18, body 14 still being colored differently than body 18. Further, tablet 10 may be a combination of fast and sustained release excipients such as croscarmelose in body 14 and high molecular weight hydroxypropyl methylcellulose in body 18, body 14 being colored differently than body 18 or, alternatively, body 14 being colored the same as body 18, and body 14 containing the same or different active substance than body 18. The coloring agents employed are conventional. In one embodiment body 14 was red while body 18 was yellow. Any desired color combination, however, can be employed. Also, the tablet can be formed in multiple segments of different size instead of equal halves.

Figure 3:
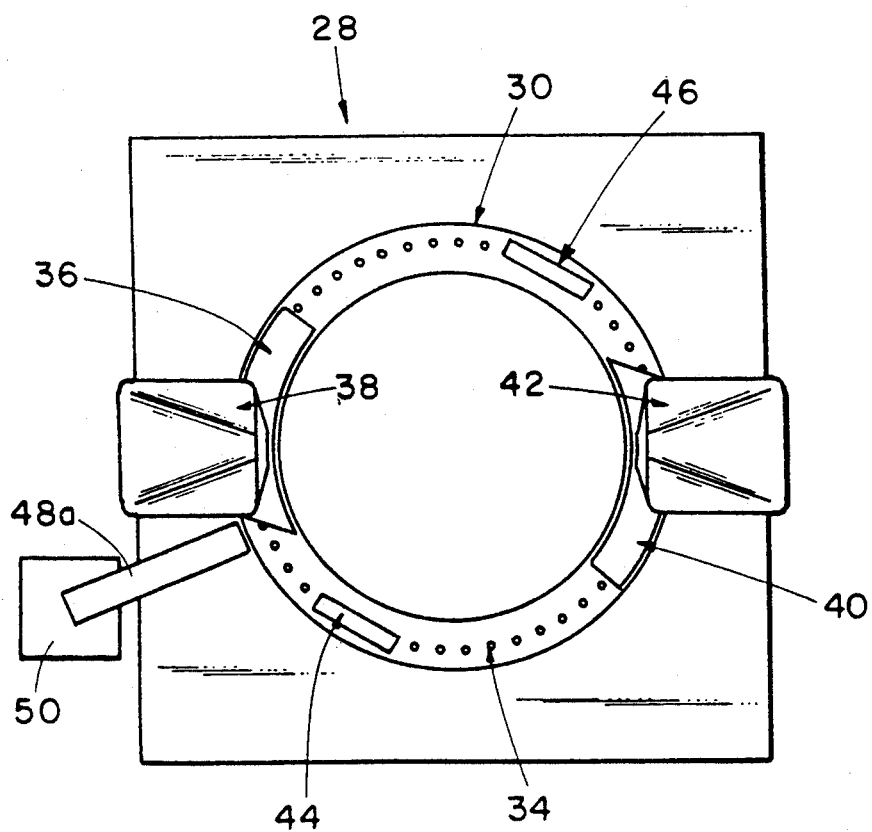
FIG. 3 is a plan view of a double rotary press.
Figure 4:
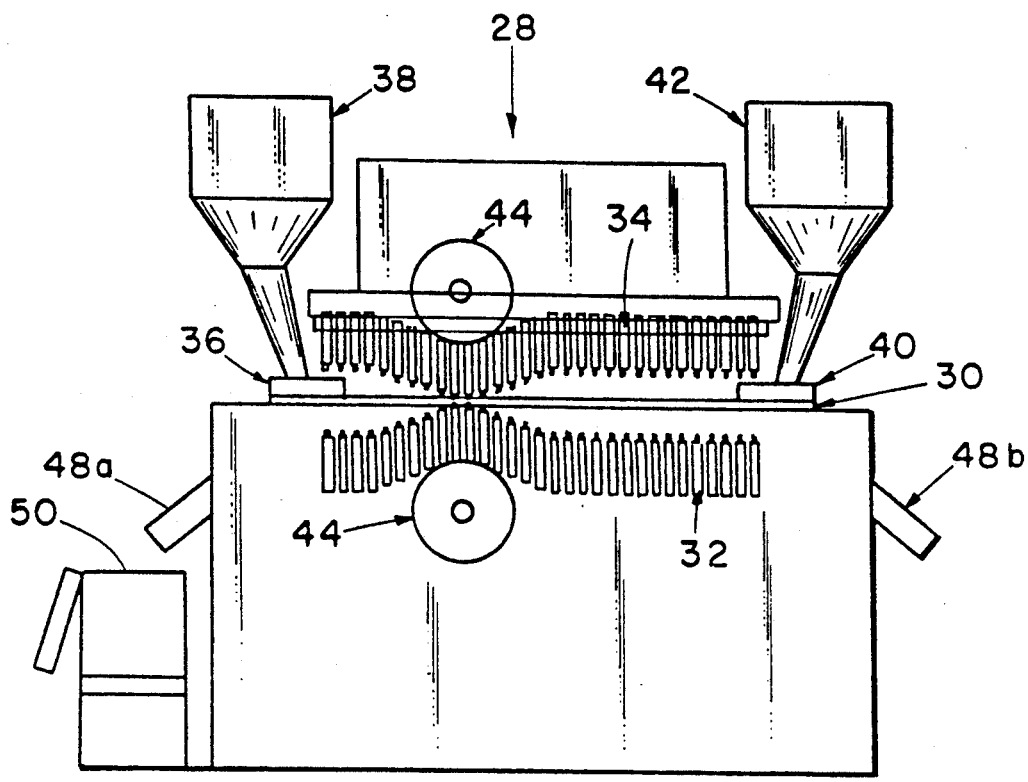
FIG. 4 is an elevational view of the double rotary press of FIG. 3.

FIGS. 3 and 4 illustrate, generally, a Stokes DD2 double-sided rotary press modified to accommodate bi-layer tablet manufacture. The direction of rotation is clockwise as viewed in FIG. 3. FIG. 4 is an elevational view of the press 28 illustrating a series of lower punches 32 positioned below a rotary die table 30 and a series of upper punches 34 located above the die table 30. Rotary die table 30 includes a plurality of die cavities 31 (FIG. 5) arrayed in a circle near the perimeter of table 30, each being positioned below a corresponding upper punch 34. Upper and lower punches 32 and 34 move in a circle in conjunction with rotary die table 30 such that a given lower punch 32 and a given upper punch 34 are always aligned with a corresponding die cavity 31.

A first feed frame 36, with a hopper 38, is positioned on rotary die table 30 opposite a second feed frame 40, which also has a hopper 42. A pair of compression wheels 44 (FIGS. 3 and 4) are located at the front of press 28. A pair of compression wheels 46, located at the rear of the press 28, have been modified such that they provide basically only the weight of the upper punch to tamp or level any formulation located within the die table 30. The term level is used in a general sense in that the first powder is "level" at a circumferential line of demarcation. However, the powder 38A is actually rounded upwardly slightly above the level of demarcation due to the concave shape of the bottom of upper punches 34. A tablet chute 48A provides the route by which the completed bi-layer tablets are ejected from the press 28 into a bulk tablet storage container 50.

Figure 5:
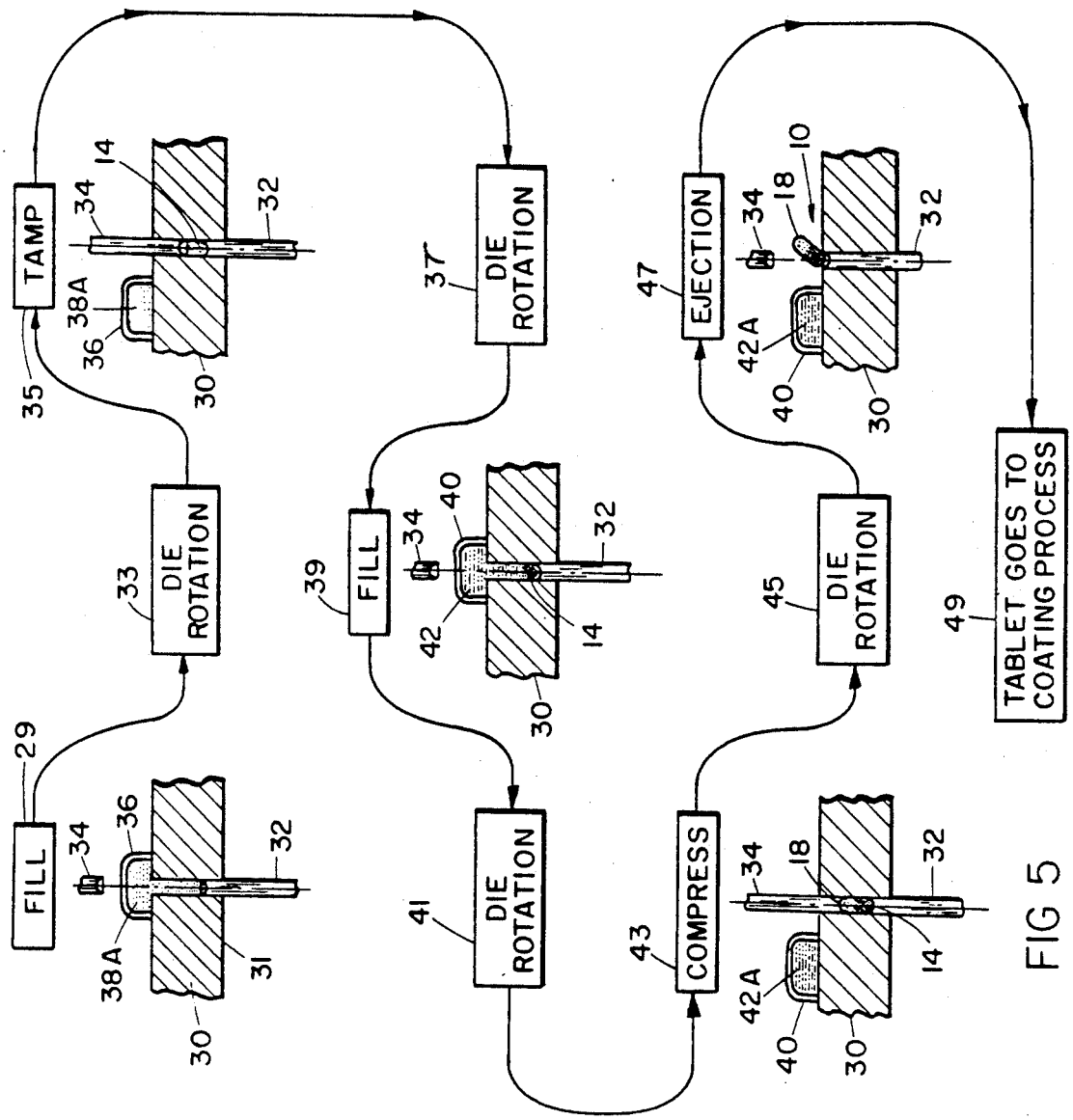
FIG. 5 is a diagrammatic view of the manufacturing equipment and sequence for producing the core of the bi-layer tablet shown in FIGS. 1 and 2.

The first step in the manufacturing process illustrated in FIG. 5 is die filling 29 where the material 38A to be compressed is transferred by gravity, or induced flow from feed frame 36, to a die cavity 31. At one end of the die cavity 31 is the lower punch 32 and positioned above the die cavity 31 and above feed frame 36 is the upper punch 34. Upper punch 34 and lower punch 32 each have concave facings which give the tablet 10 its characteristic hemispherical caps. Lower punch 32 is positioned at its lowest point in die cavity 31 to receive first powder 38A. The first powder 38A consists of a first blend of excipients, active substances and a first coloring agent. Following the filling of the die cavity 31 with the first powder 38A, the die table 30 continues rotation as indicated by block 33 to position a new die under the feed frame 36 to fill the new die with the first powder 38A, and partially filled die 30 proceeds to tamping station 35. As die table 30 continues to rotate, lower punch 32 rides over a first weight adjustment cam (not shown) which regulates the amount of first powder 38A in die cavity 31. If too much first powder 38A has been added to die cavity 31, the first weight adjustment cam forces lower punch 32 up into die cavity 31 so that the excess first powder 38A can be scraped off by first feed frame 36. After scraping, lower punch 32 drops back down to a lower neutral position.

The next step in the manufacturing process is tamping 35 where, at compression wheels 46, the first powder 38A is tamped between the upper punch 34 and the lower punch 32 to level the first powder 38A in the die cavity 31 so as to establish the future demarcation line 22 between the first body 14 and the second body 18. The tamping is an essential step in the manufacturing process to assure that the die wall is cleaned of the first powder to avoid speckling, to provide a clear and laterally level line of demarcation 22, and to move all of the first powder 38A to a lower position in the die cavity 31 so that a proper void volume exists for second powder 42A during second die filling 39. It is important that the tamping pressure applied be sufficient to accomplish this much, but not so great as to compact first powder 38A sufficiently to hinder its ability to bind with a second powder upon final compaction. When the upper punch enters the die 30, it thus removes any residual first powder 38 from the sidewalls of the die cavity 31, which prevents contamination (i.e., speckling) of the second body 14 of the tablet 10. Following the tamping, the die table 30 continues rotation again as indicated by block 37 to position a newly filled die to the tamping step, and the first filled die cavity 31 proceeds to second die filling 39.

The second feed frame 40 is positioned over the die cavity 31 and a second powder 42A is transferred into the die cavity 31. The second powder 42A consists of a second blend of excipients, active substances and coloring agents. Following the filling of die cavity 31 with the second powder 42A on top of the first powder 38A, die table 30 continues to rotate (block 41) to position a new die cavity under the second feed frame 40 to receive the second powder 42A, and the first filled die cavity 31 proceeds to final compression 43. As die table 30 continues to rotate, lower punch 32 rides over a second weight adjustment cam (not shown) which regulates the amount of second powder 42A in die cavity 31. As with the first die filling 29, if too much second powder 42A has been added to die cavity 31, the second wight adjustment cam forces lower punch 32 up into die cavity 31 so that the excess second powder 42A can be scraped off by second feed frame 40.

In final compression 43, the first powder 38A and the second powder 42A are compressed between the upper punch 34 and the lower punch 32 to form the tablet 10. Compression of the upper punch 34 and the lower punch 32 is achieved by means of compression wheels 44 (FIGS. 3 and 4). The pressure applied ranges from 0.5 to 2 tons, with 1 ton being preferred for this example. It is also preferred that the vertical axes of compression wheels, which pass through the axis of rotation of wheels 44, be offset up to 2 inches so sa to maximize the rate of production and to facilitate uniformity of hardness throughout the capsule-shaped tablet. Following final compression, die table 30 continues to rotate (block 45) the following die cavity for the final compression step and ejects (block 47) the formed bi-layer tablet 10 from the die cavity 31 into tablet chute 48A and bulk tablet storage container 50.

The compression of the multi-colored, bi-layer capsule-like tablet 10 along the longitudinal axis requires the use of a die with a deep draft or deep depth of fill. The use of such dies, however, exacerbates the problem of the formulation sticking to the sidewall of the die. To prevent sidewall sticking, a formulation of appropriate lubricity must be used. An appropriate lubricity level means the compressed mix does not adhere or stick to either die wall or punch face. The lubricity may be contributed by mix ingredients (e.g., starch, talc, microcrystalline cellulose etc.) and/or by specific pharmaceutical lubricants such as stearic acid, magnesium stearate, sodium lauryl sulfate and others. In addition, some active ingredients such as acetylsalicylic acid, possess natural lubrication characteristics which contribute lubricity to the mix.

A feature of the present invention is to coat the bi-layer, two colored tablet 10 with a single coating of gelatin or a film forming polymeric substance which will simulate the appearance and function of a gelatin capsule. This step is illustrated by block 49 of FIG. 5. A number of film forming materials are known in this art which will serve this purpose. By way of example, the following may be employed: methylcellulose, hydroxypropyl methylcellulose (PHARMACOAT 606 6 cps), polyvinylpyrrolidone (Povidone), ethylcellulose (ETHOCEL 10 cps), various derivatives of methacrylic acids and methacrylic acid esters, and cellulose acetate phthalate.

The thickness of the coating of the film forming polymer that is applied to the capsule-shaped tablet of this invention may vary. The only essential limit is that it be able to simulate the appearance, feel (tactile and mouth feel) and function of a gelatin capsule. In the case where quick or delayed absorption of the active pharmaceutical agents contained in the tablet is desired, this will be taken into account in determining the type and thickness of the film coating.

The coating of the film forming polymer may be applied to the capsule-shaped tablets according to the present invention in a number of ways. The film coating may be performed using any one of several types of equipment such as a conventional coating pan, Accela-Cota, High-Cota or Wurster air suspension column. Such equipment typically has an exhaust system to remove dust and solvent or water vapors to facilitate quick drying. Spray guns or other suitable atomizing equipment may be introduced into the coating pans to provide spray patterns conducive to rapid and uniform coverage of the tablet bed. Normally, heated or cold drying air is introduced over the tablet bed in a continuous or alternate fashion with a spray cycle to expedite drying of the solution.

The coating solution may be sprayed by using positive pneumatic displacement or peristaltic spray pump systems in a continuously or intermittent spray-dry cycle. The particular type of spray application is selected depending upon the drying efficiency of the coating pan.

In most cases, the coating material is sprayed until the tablets are uniformly coated to the desired thickness and the desired appearance of the tablet is achieved. Many different types of coatings may be applied such as enteric, slow release or rapidly dissolving type for fast acting tablets. The polymeric film coating applied to the capsule-shaped tablets according to the present invention is designated as 24 in FIG. 2. The relative thickness of coating 24 is somewhat exaggerated so that it can be seen in the drawing.

The Stokes DD2 rotary press is capable of producing a tablet equivalent to a two-piece, hard shell gelatin capsule size No. 2. During this production it is suggested that a vacuum block be used to prevent co-mingling of powders on feed frames. In order to make a tablet equivalent to a two-piece, hard shell gelatin capsule size No. 1, a modified Hata 30 ton, 18 station rotary press, Model HT-B18-EH3, manufactured by Elizabeth Hata Corp., North Huntington, Pa., is suggested because the Hata press has a depth of fill of at least 47 mm. Because the Hata press generally has a deeper draw than most pharmaceutical rotary tablet presses, it is better able to produce a tablet equivalent to a hard shell gelatin capsule size No. 1. The success of the tamping step is contingent upon the ability of the upper punch or the tamping used to penetrate the die far enough to level the first fill. Modification of the upper punch or tamping rod may be required to properly tamp and level the first fill. Also, when producing the bi-layered tablet with either a Stokes or Hata press, basically only the weight of the punch, or an equivalent thereof, is used for the tamping step. Too much compaction of the first fill will hinder its ability to properly bind with the second fill upon final compression.

Figure 6:
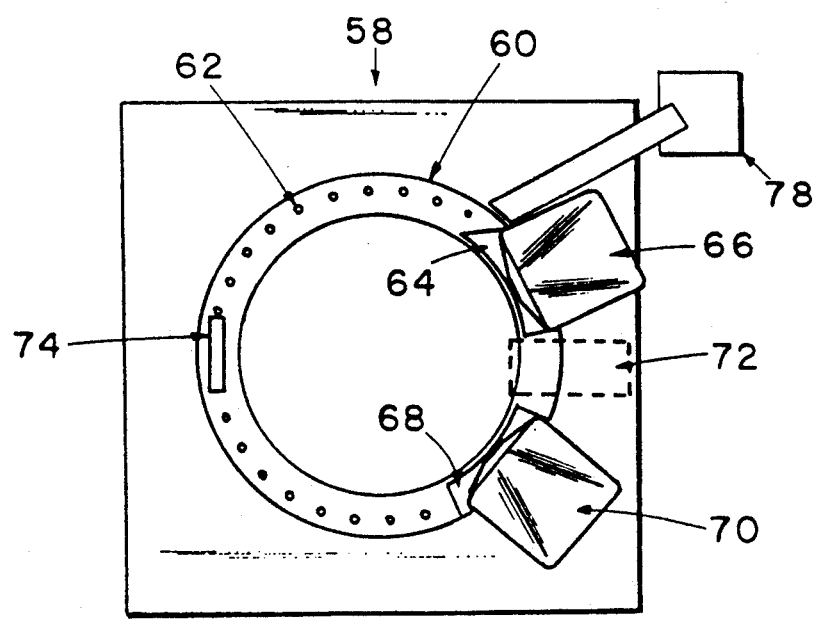
FIG. 6 is a plan view of a single rotary press modified for bi-layer tablet production.

FIG. 6 illustrates, generally, a single rotary press 58 which has been modified to accommodate bi-layer tablet manufacture. FIG. 6 is a plan view of press 58 illustrating a series of upper punches 62 located above a die table 60. A first feed frame 64, with a hopper 66 and a second feed frame 68, with a hopper 70 are positioned serially on rotary die table 60. Positioned between the first feed frame 64 and the second feed frame 68 is a tamping zone 72. Opposite the tamping zone 72 is a compression wheel 74. A tablet chute 76 provides the route by which the completed bi-layer capsule-shaped tablets ejected from the rotary die table 60 are removed from the press 58 into a bulk tablet storage container 78.

The manufacturing process described above with respect to FIG. 5 is essentially the process that would be followed to manufacture bi-layer tablets on press 58. The only notable differences is that press 58, being a single rotary press, would require that some form of tamping mechanism be attached to the press, whereas press 28 merely modified the second set of compression wheels 46.

The following examples are given to further illustrate the present invention. It is to be understood, however, that this invention is not limited thereto.

EXAMPLE 1

Two-Colored, Bi-Layer Capsule-Shaped Tablet Fabrication

INTRODUCTION

A bi-layer capsule-shaped tablet is made from two separate layers which were compressed together on a tablet press to form a tablet with an appearance similar to a capsule's appearance.

| Material | Percent |
|---|---|
| PREPARATION OF LAYER A: | |
| Layer A was composed of the following ingredients: | |
| Direct Compression Acetaminophen* | 95.69 |
| D&C Yellow Aluminum Lake #10 | 0.34 |
| Croscarmelose, NF | 2.00 |
| Stearic Acid, NF | 2.00 |
| PREPARATION OF LAYER B: | |
| Layer B was composed of the following ingredients: | |
| Acetaminophen, NF 60 mesh | 77.8 |
| D&C Red Aluminum Lake #30 | 8.9 |
| F,D&C Red Aluminum Lake #40 | 1.0 |
| Starch 1551 | 7.0 |
| Polyvinylpyrrolidone, USP | 1.0 |
| Stearic Acid, NF | 3.0 |

*Direct compression Acetaminophen contains 90% Acetaminophen, 10% starch. All of the ingredients of Layer A were blended together.

The materials of Layer B were granulated in a Fielder granulator unit. A portion of the Starch 1551 and all of the Polyvinylpyrrolidone was dissolved in water to form a binding solution. The dry raw materials except for stearic acid were placed in a Fielder granulator and vigorously mixed while the binding solution was atomized through a nozzle and sprayed onto the dry materials. After all of the solution was applied and granules were formed, the wetted mass was transferred to a Glatt fluid bed granulator where it was dried using fluidization with warm air. At the end of the drying cycle the material was size discriminated using a Sweco sieving unit. The stearic acid, NF, was blended into the granulation after the sieving step was completed.

Layer B may also be prepared by fluidized bed granulation. The binding solution is the same as is used for a Fielder granulation. All of the dry raw materials except for stearic acid are placed in a Glatt fluid bed granulator and are fluidized with heated air while binding solution is atomized through a nozzle as it is sprayed onto the fluidized powders. Granules are formed as the powders are wetted. After all of the binding solution is applied the granulation is dried in the Glatt granulator. The granulation is size discriminated through a Sweco sieving unit. The stearic acid, NF, is blended into the granulation after the sieving step is completed. Stearic acid, NF, is added to the granulation in an amount between 2% to 4% in order to prevent particles from sticking to the sidewalls of the dies or punch faces.

PREPARATION OF THE TABLET CORE

A Stokes DD2 tablet press was used to make the bi-layer tablets. The press has two separate hoppers and feed frames. The first hopper was filled with Layer A and the second hopper was filled with Layer B. The feed frames do not recirculate Layers A or B. A station on the press is composed of a lower punch, a die and an upper punch. At each station, a lower punch is fitted into the die cavity. The upper punch moves in and out of the die cavity to compress tablets, to allow tablet ejection and to allow the die cavities to be filled with powder.

The tooling used was ¼ inch round concave, with 0.075 inch cup depth. A die cavity on the tablet press moved under the first hopper and was filled with about 270 mg of Layer A. As this filled die cavity continued to move, the lower punch dropped, which lowered the height of Layer A in the die cavity. Layer A was added first because any particles remaining on the sidewalls of the die were tamped down during the tamping step. The die cavity partially filled with Layer A moved under the second hopper and feed frame and was filled with about 270 mg of Layer B. The two layers were compressed into one tablet. The tablet had two distinct layers which were intimately bonded together.

The average tablet weight was 537 mg per tablet, while the tablet hardness ranged from 8 to 11 SCU. The average tablet friability was 0.3% weight loss over 6 minutes and the disintegration time was approximately 15 minutes.

The next step is a routine coating step which was not done for the purpose of this or the following examples.

EXAMPLE 2

Monochromatic. Bi-layered, Buffered Aspirin Tablet

A bi-layered, monochromatic, capsule-shaped tablet was made in the same manner as in Example 1 to demonstrate the invention using different powders. Coloring was left out of this demonstration.

| | Standard Tablet percent | Capsule-Shaped Tablet percent |
|---|---|---|
| Aspirin Layer (filled first) | | |
| Aspirin, 20 mesh | 85.75 | 84.89 |
| Microcrystalline Cellulose | 7.65 | 7.58 |
| Cabosil M5 | 0.79 | 0.78 |
| Crospovidone | 1.32 | 1.31 |
| Talc | 4.49 | 4.44 |
| Stearic Acid | 0 | 1.00 |
| Buffer Layer (filled second) | | |
| Calcium Carbonate | 56.62 | 55.20 |
| Magnesium Oxide powder | 21,16 | 20.63 |
| Magnesium Carbonate | 12.87 | 12.55 |
| Citric Acid, Anhydrous | 2.27 | 2.21 |
| Starch, NF | 5.75 | 5.61 |
| Simethicone Emulsion, LS | 0.33 | 0.32 |
| Magnesium Stearate | 0.99 | 0.97 |
| Stearic Acid | 0 | 2.50 |

The tablet hardness was around 15.5 SCU while the average tablet friability was 0.5% loss over 6 minutes and the disintegration time was approximately 15 minutes.

The foregoing detailed description is given for clearness of understanding only, and no unnecessary limitations should be implied. Various modifications to the preferred embodiments described herein can be made by those skilled in the art without departing from the spirit or scope of the invention as defined by the appended claims.

The embodiments of the invention in which an exclusive property or privilege is claimed are defined as follows:

1. A method of manufacturing a pharmaceutical tablet comprising:

filling a die cavity partially with a first blend of solid particulate excipients and active substances, and a first coloring agent;

leveling said first blend in said die cavity and clearing the walls of said die cavity above said first blend to define a clear line of demarcation at the upper circumferential edge of said first blend;

filling the unfilled portion of said die cavity with a second blend of solid particulate excipients and active substances, and a second coloring agent;

compressing said first blend and said second blend along the longitudinal axis of said die cavity to form a layered capsule-shaped tablet; and removing the capsule-shaped tablet from the die cavity.

2. The method of claim 1 which includes coating said tablet with a clear coating.

3. The method of claim 1 in which said step of leveling said first blend in said die cavity comprises making said first blend level at its line of demarcation with said second blend, but rounding said first blend upwardly slightly above said line of demarcation.

4. A method of manufacturing a pharmaceutical tablet comprising:

filling a die cavity partially with a first blend of solid particulate excipients and active substances, and a first coloring agent;

rotating the die cavity on a rotary press;

leveling said first blend in said die cavity and clearing the walls of said die cavity above said first blend to define a clear line of demarcation at the upper circumferential edge of said first blend;

rotating said die cavity on said rotary press;

filling the unfilled portion of said die cavity with a second blend of solid particulate excipients and active substances, and a second coloring agent;

rotating said die cavity on said rotary press;

compressing said first blend and said second blend between a lower punch and an upper punch along the longitudinal axis of said die cavity to form a layered capsule-shaped tablet;

rotating said die cavity on said rotary press; and ejecting the layered capsule-shaped tablet from the rotary press.

5. The method of claim 4 which includes coating the layered capsule-shaped tablet with a clear coating.

6. The method of claim 4 in which said step of leveling said first blend in said die cavity comprises making said first blend level at its line of demarcation with said second blend, but rounding said first blend upwardly slightly above said line of demarcation.

7. A method of manufacturing a pharmaceutical tablet comprising:

filling a die cavity partially with a first blend of solid particulate excipients and active substances, including a first distinguishing ingredient;

leveling said first blend in said die cavity and clearing the walls of said die cavity above said first blend to define a clear line of demarcation at the upper circumferential edge of said first blend;

filling the unfilled portion of said die cavity with a second blend of solid particulate excipients and active substances, including a second distinguishing ingredient;

compressing said first blend and said second blend along the longitudinal axis of said die cavity to form a layered capsule-shaped tablet; and removing the capsule-shaped tablet from the die cavity.

8. The method of claim 7 and further including coating said tablet with a clear coating.

9. The method of claim 7 and further including:

regulating the amount of said first blend in said dei cavity by movably positioning a lower punch in said cavity and forcing said lower punch supporting said first blend up into said die cavity to force excess of said first blend out of the open top of said cavity where it is easily removed;

moving said lower punch to a lower position within said die cavity; and regulating the amount of said second blend in said die cavity by forcing said lower punch supporting said first blend and said second blend up into said die cavity to force the excess of said second blend out of said open top of said cavity where it is easily removed.

10. The method as defined in claim 7 wherein said excipients and active substances are granules or microgranules.

11. The method as defined in claim 7 wherein said first and second blends are filled into said cavity to substantially equal depths.

12. The method as defined in claim 7 wherein said first and second distinguishing ingredients are different excipients which control the release of said one or more active substances.

13. The method as defined in claim 12 wherein at least one of said first and second blends of excipients retards the release of said one or more active substances.

14. The method as defined in claim 7 wherein said blend of excipients and active substances has a lubricity level sufficient to avoid sidewall sticking in a tablet compression die.

15. The method as defined in claim 7 wherein said sufficient lubricity level is obtained by adding a pharmaceutical grade lubricant to said blend of excipients and active substances.

16. The method of claim 15 wherein said lubricant is selected from one or more of the following ingredients: starch, talc, microcrystalline cellulose, stearic acid, magnesium stearate, sodium lauryl sulfate and acetylsalicylic acid.

17. The method of claim 15 wherein said lubricant is selected from one or more of the following ingredients: stearic acid, magnesium stearate, and sodium lauryl sulfate.

18. The tablet as defined in claim 14 wherein said lubricity level is obtained by the natural lubricity of said blend of excipients and active substances.

19. The method of claim 7 in which said step of leveling said first blend in said die cavity comprises making said first blend level at its line of demarcation with said second blend, but rounding said first blend upwardly slightly above said line of demarcation.

20. The method of claim 9 in which said step of leveling said first blend in said die cavity comprises making said first blend level at its line of demarcation with said second blend, but rounding said first blend upwardly slightly above said line of demarcation.

21. A method of manufacturing a pharmaceutical tablet comprising:

filling a die cavity partially with a first blend of solid particulate excipients and active substances, including a first distinguishing ingredient;

rotating the die cavity on a rotary press;

leveling said first blend in said die cavity and clearing the walls of said die cavity above said first blend to define a clear line of demarcation at the upper circumferential edge of said first blend;

rotating said die cavity on said rotary press;

filling the unfilled portion of said die cavity with a second blend of solid particulate excipients and active substances, including a second distinguishing ingredient;

rotating said die cavity on said rotary press;

compressing said first blend and said second blend between a lower punch and an upper punch along the longitudinal axis of said die cavity to form a layered capsule-shaped tablet;

rotating said die cavity on said rotary press; and ejecting the layered capsule-shaped tablet from the rotary press.

22. The method of claim 21 and further including coating the layered capsule-shaped tablet with a clear coating.

23. The method of claim 21 and further including:

regulating the amount of said first blend in said dei cavity by movably positioning a lower punch in said cavity and forcing said lower punch supporting said first blend up into said die cavity to force excess of said first blend out of the open top of said cavity where it is easily removed;

moving said lower punch to a lower position within said die cavity; and regulating the amount of said second blend in said die cavity by forcing said lower punch supporting said first blend and second blend up into said die cavity to force the excess of said second blend out of said open top of said cavity where it is easily removed.

24. The method as defined in claim 21 wherein said excipients and active substances are granules or microgranules.

25. The method as defined in claim 21 wherein said first and second blends are filled into said cavity to substantially equal depths.

26. The method as defined in claim 21 wherein said first and second distinguishing ingredients are different excipients which control the release of said one or more active substances.

27. The method as defined in claim 26 wherein at least one of said first and second blends of excipients retards the release of said one or more active substances.

28. The method as defined in claim 21 wherein said blend of excipients and active substances has a lubricity level sufficient to avoid sidewall sticking in a tablet compression die.

29. The method as defined in claim 28 wherein said sufficient lubricity level is obtained by adding a pharmaceutical grade lubricant to said blend of excipients and active substances.

30. The method of claim 29 wherein said lubricant is selected from one or more of the following ingredients: starch, talc, microcrystalline cellulose, stearic acid, magnesium stearate, sodium lauryl sulfate and acetylsalicylic acid.

31. The method of claim 29 wherein said lubricant is selected from one or more of the following ingredients: stearic acid, magnesium stearate, and sodium lauryl sulfate.

32. The tablet as defined in claim 28 wherein said lubricity level is obtained by the natural lubricity of said blend of excipients and active substances.

33. The method of claim 21 in which said step of leveling said first blend in said die cavity comprises making said first blend level at its line of demarcation with said second blend, but rounding said first blend upwardly slightly above said line of demarcation.

34. The method of claim 23 in which said step of leveling said first blend in said die cavity comprises making said first blend level at its line of demarcation with said second blend, but rounding said first blend upwardly slightly above said line of demarcation.

35. A method of manufacturing a pharmaceutical tablet comprising:

filling a die cavity partially with a first blend of solid particulate excipients and active substances, including a first distinguishing ingredient;

leveling said first blend in said die cavity;

filling the unfilled portion of said die cavity with a second blend of solid particulate excipients and active substances, including a second distinguishing ingredient;

compressing said first blend and said second blend along the longitudinal axis of said die cavity to form a layered capsule-shaped tablet; and removing the capsule-shaped tablet from the die cavity.

36. The method of claim 35 and further including:

regulating the amount of said first blend in said dei cavity by movably positioning a lower punch in said cavity and forcing said lower punch supporting said first blend up into said die cavity to force excess of said first blend out of the open top of said cavity where it is easily removed;

moving said lower punch to a lower position within said die cavity; and regulating the amount of said second blend in said die cavity by forcing said lower punch supporting said first blend and said second blend up into said die cavity to force the excess of said second blend out of said open top of said cavity where it is easily removed.

37. The method as defined in claim 36 wherein said excipients and active substances are granules or microgranules.

38. The method as defined in claim 37 wherein said first and second blends are filled into said cavity to substantially equal depths.

39. The method as defined in claim 38 wherein said blend of excipients and active substances has a lubricity level sufficient to avoid sidewall sticking in a tablet compression die.

40. The method as defined in claim 39 wherein said sufficient lubricity level is obtained by adding a pharmaceutical grade lubricant to said blend of excipients and active substances.

41. The method of claim 40 wherein said lubricant is selected from one or more of the following ingredients: starch, talc, microcrystalline cellulose, stearic acid, magnesium stearate, sodium lauryl sulfate and acetylsalicylic acid.

42. The method of claim 40 wherein said lubricant is selected from one or more of the following ingredients: stearic acid, magnesium stearate, and sodium lauryl sulfate.

43. The method of claim 35 in which said step of leveling said first blend in said die cavity comprises making said first blend level at its line of demarcation with said second blend, but rounding said first blend upwardly slightly above said line of demarcation.

44. The method of claim 36 in which said step of leveling said first blend in said die cavity comprises making said first blend level at its line of demarcation with said second blend, but rounding said first blend upwardly slightly above said line of demarcation.

* * * * *

UNITED STATES PATENT AND TRADEMARK OFFICE
CERTIFICATE OF CORRECTION

PATENT NO. : 5,213,738
DATED : May 25, 1993
INVENTOR(S) : Douglas B. Hampton, et al.

It is certified that error appears in the above-indentified patent and that said Letters Patent is hereby corrected as shown below:

Column 5, Line 4:

"wight" should be --weight--;

Column 5, Line ]6:

"so sa" should be --so as--;

Column 8, Line 47-1/2:

"21,16" should be --21.16--;

Column 10, Line 9, Claim 9:

"said dei" should be --said die--;

Column 11, Line 26, Claim 23:

"said dei" should be --said die--;

Column 11, Line 27, Claim 23:

"a lower" should be --said lower--;

UNITED STATES PATENT AND TRADEMARK OFFICE
CERTIFICATE OF CORRECTION

PATENT NO. : 5,213,738
DATED : May 25, 1993
INVENTOR(S) : Douglas B. Hampton, et. al.

It is certified that error appears in the above-indentified patent and that said Letters Patent is hereby corrected as shown below:

Column 12, Line 30, Claim 36:

"said dei" should be --said die--.

Signed and Sealed this

Twenty-sixth Day of April, 1994

Attest:

BRUCE LEHMAN

Attesting Officer    Commissioner of Patents and Trademarks